United States Patent [19]

Willard et al.

[11] Patent Number: 5,222,971
[45] Date of Patent: Jun. 29, 1993

[54] TEMPORARY STENT AND METHODS FOR USE AND MANUFACTURE

[75] Inventors: Lloyd Willard, Miltona; Dale F. Schmaltz, St. Paul, both of Minn.

[73] Assignee: Scimed Life Systems, Inc., Maple Grove, Minn.

[21] Appl. No.: 594,121

[22] Filed: Oct. 9, 1990

[51] Int. Cl.$^5$ ............................................. A61M 29/00
[52] U.S. Cl. .................................. 606/158; 606/200; 604/104
[58] Field of Search ............... 606/191, 192, 194, 195, 606/196, 197, 198; 604/95-106; 128/898; 623/1, 12

[56] References Cited

U.S. PATENT DOCUMENTS

| | | | |
|---|---|---|---|
| 2,836,181 | 5/1958 | Tapp | 128/334 |
| 3,509,883 | 5/1970 | Dibelius | 128/348 |
| 3,663,288 | 5/1972 | Miller | 117/7 |
| 3,868,956 | 3/1975 | Alfidi et al. | 128/345 |
| 3,996,938 | 12/1976 | Clark, III | 128/348 |
| 4,046,150 | 9/1977 | Schwartz et al. | 128/328 |
| 4,140,126 | 2/1979 | Choudhury | 128/325 |
| 4,307,722 | 12/1981 | Evans | 128/344 |
| 4,326,532 | 4/1982 | Hammar | 128/349 |
| 4,347,846 | 9/1982 | Dormia | 128/328 |
| 4,434,797 | 3/1984 | Silander | 128/343 |
| 4,503,569 | 3/1985 | Dotter | 3/1.4 |
| 4,512,338 | 4/1985 | Balko et al. | 128/1 R |
| 4,553,545 | 11/1985 | Maass et al. | 128/341 |
| 4,572,186 | 2/1986 | Gould et al. | 128/341 |
| 4,580,568 | 4/1986 | Gianturco | 128/345 |
| 4,629,458 | 12/1986 | Pinchuk . | |
| 4,649,922 | 3/1987 | Wiktor | 128/344 |
| 4,650,466 | 3/1987 | Luther | 604/95 |
| 4,655,771 | 4/1987 | Wallsten | 623/1 |
| 4,656,083 | 4/1987 | Hoffman et al. | 428/265 |
| 4,713,402 | 12/1987 | Solomon | 523/112 |
| 4,723,549 | 2/1988 | Wholey et al. | 128/344 |
| 4,733,665 | 3/1988 | Palmaz | 128/343 |
| 4,739,762 | 4/1988 | Palmaz | 128/343 |
| 4,768,507 | 9/1988 | Fischell et al. | 128/303 R |
| 4,773,432 | 9/1988 | Rydell | 128/772 |
| 4,776,337 | 10/1988 | Palmaz | 128/343 |
| 4,795,458 | 1/1989 | Regan | 623/1 |
| 4,800,882 | 1/1989 | Gianturco | 128/343 |

(List continued on next page.)

FOREIGN PATENT DOCUMENTS

| | | |
|---|---|---|
| 0321912A1 | 6/1989 | European Pat. Off. . |
| 0382014A1 | 8/1990 | European Pat. Off. . |
| 0433011A1 | 6/1991 | European Pat. Off. . |
| 3107392A1 | 9/1982 | Fed. Rep. of Germany . |
| 9010130.8 | 10/1990 | Fed. Rep. of Germany . |
| 2580504A1 | 10/1986 | France . |
| 2652267A1 | 3/1991 | France . |
| WO87/04935 | 8/1987 | PCT Int'l Appl. . |
| 2020557A | 11/1979 | United Kingdom . |
| 2020557A | 11/1979 | United Kingdom . |

OTHER PUBLICATIONS

Steven W. Werns, M.D. and Eric J. Topol. M.D., "Review of Hardware for PTCA", University of Michigan Medical School, Ann Arbor, Michigan, Jun. 30, 1988.
Ulrich Sigwart, "The Self-Expanding Mesh Stent", Section IV—Chapter 29.

*Primary Examiner*—C. Fred Rosenbaum
*Assistant Examiner*—William W. Lewis
*Attorney, Agent, or Firm*—Willian Brinks Olds Hofer Gilson & Lione

[57] ABSTRACT

A temporary stent for supporting a region of a vessel in a body comprising a stent portion and an actuator portion and methods for the use and manufacture thereof. The stent portion is comprised of an elongate perfusable vessel supporting portion adapted to be configurable between a reduced size for placement in the vessel and removal therefrom and an expanded size for structurally supporting the vessel and perfusable end portions connected to and forming ends of the vessel supporting portion and adapted to allow fluid flow therethrough. The actuator portion includes a proximal end extending out of the body and a distal end connected to the stent portion and operable by manipulation at the proximal end thereof to configure the support portion into a reduced size and an expanded size.

46 Claims, 5 Drawing Sheets

U.S. PATENT DOCUMENTS

| | | | |
|---|---|---|---|
| 4,819,751 | 4/1989 | Shimada et al. | 128/344 |
| 4,820,298 | 4/1989 | Leveen et al. | 623/1 |
| 4,848,342 | 7/1989 | Kaltenbach | 128/341 |
| 4,856,516 | 8/1989 | Hillstead | 128/343 |
| 4,871,357 | 10/1989 | Hsu et al. | 604/266 |
| 4,878,906 | 11/1989 | Lindemann et al. | 623/1 |
| 4,885,003 | 12/1989 | Hillstead | 604/22 |
| 4,895,566 | 1/1990 | Lee | 604/266 |
| 4,913,141 | 4/1990 | Hillstead | 606/108 |
| 4,921,484 | 5/1990 | Hillstead | 606/194 |
| 4,950,227 | 8/1990 | Savin et al. | 604/8 |
| 4,986,831 | 1/1991 | King et al. | 623/1 |
| 4,998,539 | 3/1991 | Delsanti | 128/898 |
| 5,002,560 | 3/1991 | Machold et al. | 604/95 |
| 5,026,377 | 6/1991 | Burton et al. | 606/108 |
| 5,034,001 | 7/1991 | Garrison et al. | 604/53 |
| 5,059,169 | 10/1991 | Zilber | 604/8 |
| 5,180,368 | 1/1993 | Garrison | 604/104 |

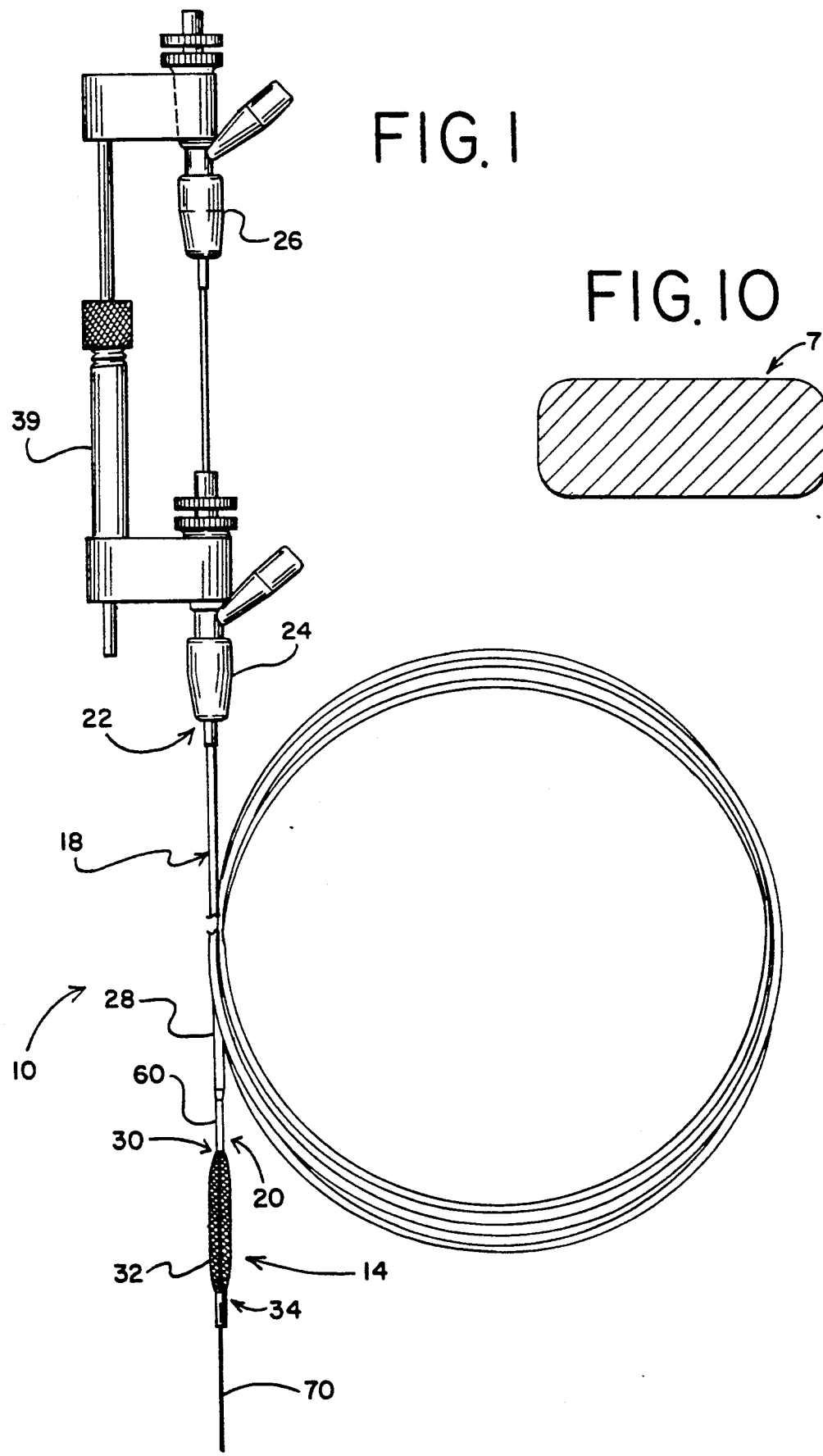

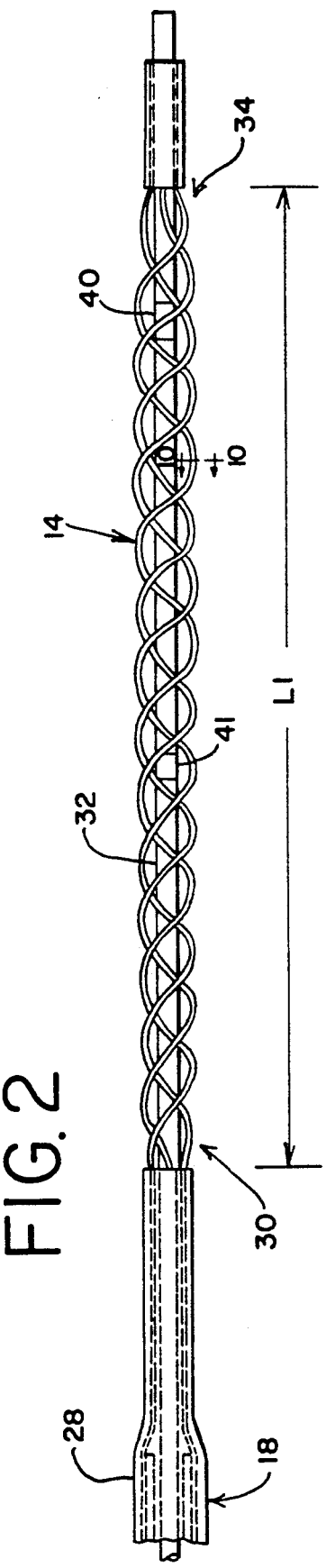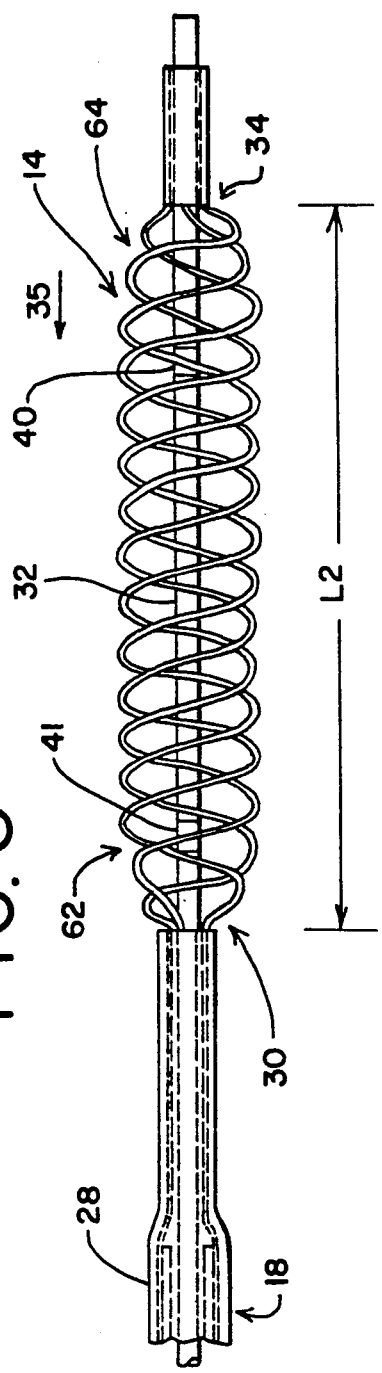

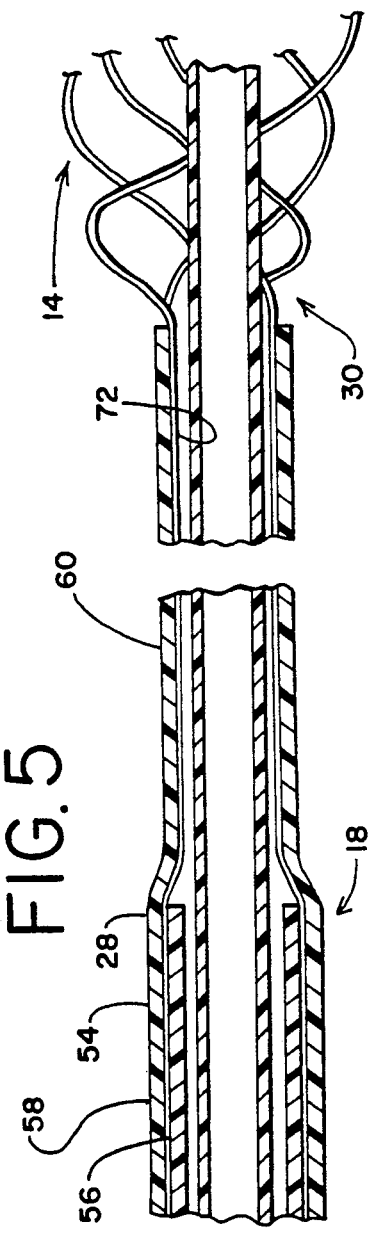
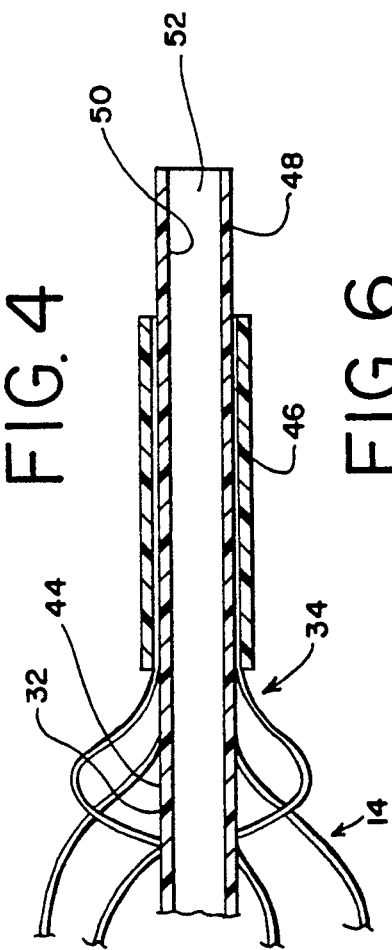
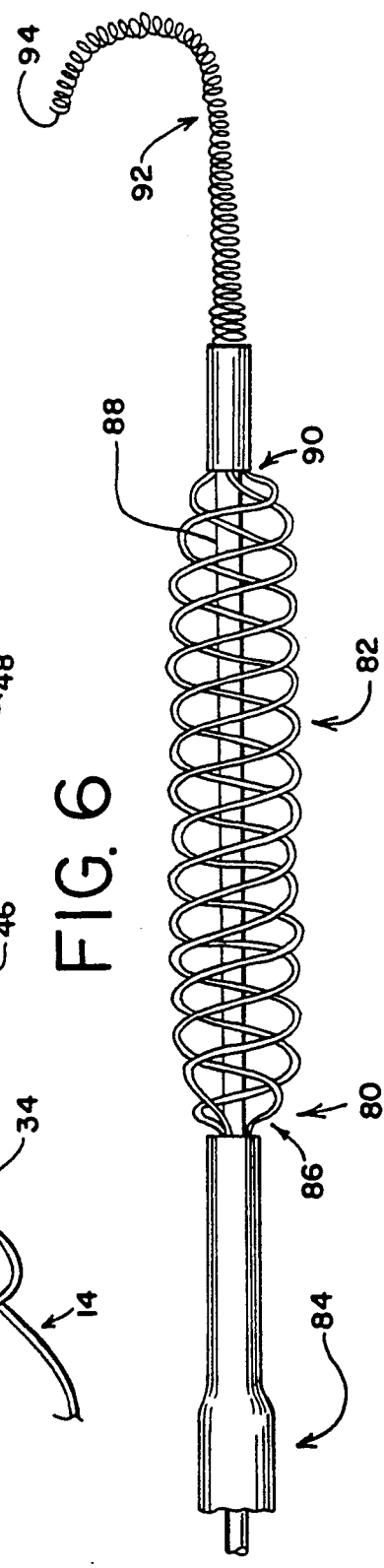

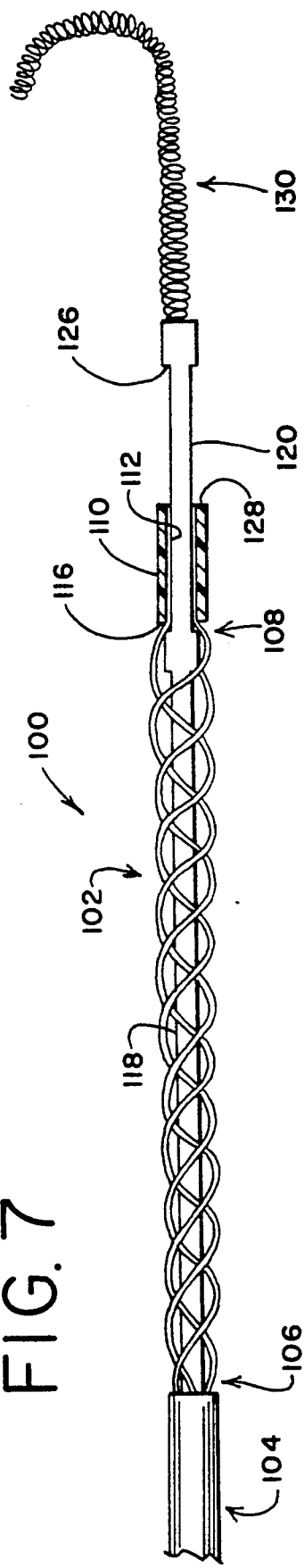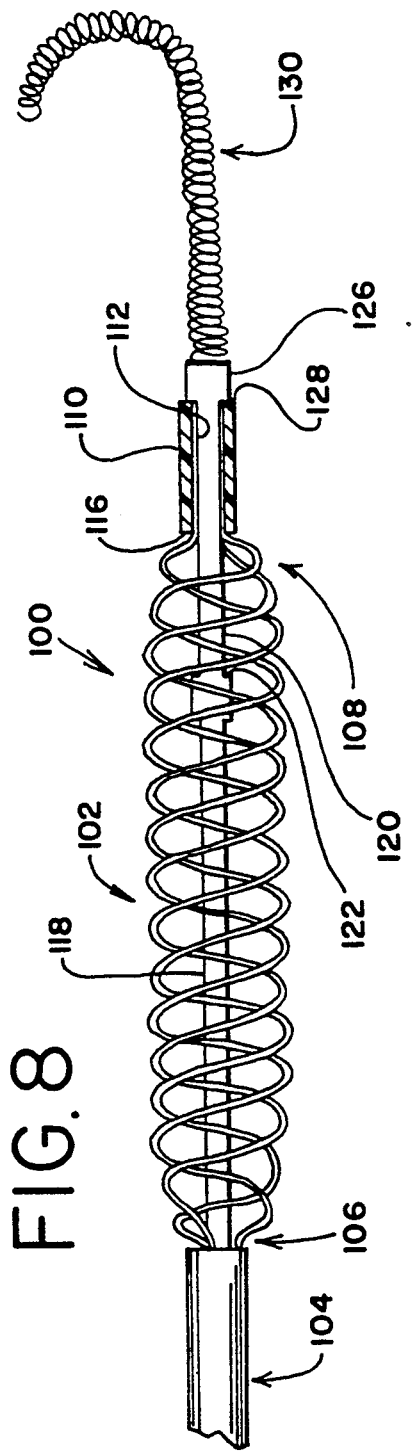
FIG. 7
FIG. 8

TEMPORARY STENT AND METHODS FOR USE AND MANUFACTURE

BACKGROUND OF THE INVENTION

This invention relates to devices known as stents which provide support to a vessel, such as a blood vessel, and in particular to stents that are both temporary and removable.

Obstructive coronary artery disease is one of most serious health problems facing our society today. This disease is the result of the deposit of fatty substances on the interior surface of the walls of the arteries. The build up or lesion of such deposits results in a narrowing of the diameter of the artery which restricts the blood flow through the artery. This condition wherein the artery is narrowed is known as stenosis. The lesion may form in any part of the artery and in some instances the deposits may form at the intersection between two arteries, that is, where the section where the two arteries form a generally "Y" configuration (e.g. bifurcate, trifurcate, and so on).

There have been significant developments of the treatment of such obstructive coronary disease in the recent past. Coronary artery bypass graft surgery is often used to treat this disease. Bypass surgery, however, has the disadvantage that it is extremely invasive and traumatic to the patient. Some of the recent developments provide a less invasive and less traumatic alternative to bypass surgery. Two of these recent developments are known as angioplasty and atherectomy procedures.

Angioplasty is a procedure in which a balloon is positioned on the inside of the artery at the site of the lesion and expanded in order to compress the materials at the lesion and thus open the restricted area in the artery. In this procedure, an elastic balloon is attached to one end of a small diameter flexible catheter which includes means for inflating the balloon from the other end of the catheter. The catheter is maneuvered through the patient's vessels to the site of the lesion with the balloon in uninflated form. When the uninflated balloon is properly positioned at the lesion, the balloon is then inflated to dilatate the restricted area.

Atherectomy is a procedure in which a small cutting tool is attached to the end of a small diameter flexible catheter and maneuvered through the patient's arterial system to the site of the lesion in the diseased artery. When the cutting tool is properly positioned, the tool is used to cut and remove the deposits from the surface of the diseased artery.

Although these two procedures provide less traumatic alternatives to bypass surgery, they are not without risk. It is possible that following procedures such as angioplasty or atherectomy the artery or blood vessel may collapse or be susceptible to constriction. In some instances it may also be necessary to abort or "bail-out" procedures such as angioplasty or atherectomy due to some type of unexpected complication.

In these situations it is necessary to maintain the integrity of the region of the artery until the artery is repaired or stabilizes. That is, following some angioplasty or atherectomy procedures or in a "bail-out" situation, it may be necessary to provide support to a artery or blood vessel on a temporary basis while there is an immediate risk that the region may collapse. This support must be provided until the region is repaired or stabilized. To provide this support, a device known as a stent may be installed at the desired region. A stent is a device which is used to hold or maintain the diameter of the artery or vessel.

Although some stents are available in the art, these are generally of the type intended for permanent use. This type of permanent stent is implanted in a patient's vascular system and remains in place after the procedure or operation. Such permanent types of stents are shown, for example, in U.S. Pat. Nos. 4,913,141, 4,878,906, 4,856,516 and 4,820,298. These permanent type of stents may not always be desired for the situations described above. First, it may be unnecessary and even undesirable to install a permanent device when only temporary support is needed. Further, these permanent type of stents may require a relatively complicated procedure to install. Further, use of permanent stents results in extended hospital observation and recovery time. Additionally, a complement of drug therapies are required in order to offset the bioreaction resulting in thrombus formation or smooth muscle cell proliferation on the stent surface. These drug therapies may be required for a significant period of time until new normal endothelial cells have formed. In situations such as a "bail-out" it is desirable for the physician to have the ability to quickly maneuver the stent to the desired location and quickly and easily place the stent in its operating mode.

A temporary stent on the other hand may be particularly useful in situations where it is intended to be used in the patient only for several minutes or days and then removed. For example, use of a temporary stent in a bail-out situation will enable the physician to defer a more complicated procedure until a patient's condition is more stable, or in some cases eliminate further procedures by resecuring the vessel geometry which allows near normal blood flow.

It is essential that a temporary stent be relatively easy to both install and remove. Since the temporary stent remains in place for a period of time, it is important that the temporary stent not block the flow of blood through the vessel. That is, the blood must be able to travel through the vessel in which the temporary stent is installed while the stent is in place. Further, since the lesions often occur at the intersection of two vessels, in order to position the temporary stent it is may be necessary to place the stent across the intersection. Therefore, it is critical that the stent provide a flow path radially as well as axially or longitudinally. This arrangement will allow blood flow to both of the intersecting arteries.

It is also desirable to have the ability to deliver medicines to the vessel either upstream or downstream of temporary stent while the stent is in place.

Since the temporary stent will be removed after a period of time, it is important that the temporary stent not permanently adhere to the inner walls of the vessel in which it is placed. In addition, a temporary stent should have no tendency, or only a minimal tendency, to cause clotting.

Accordingly, it is an object of the present invention to provide a stent that may be placed temporarily in a patient's vascular system and which is readily removable.

SUMMARY OF THE INVENTION

The present invention relates to a temporary stent for supporting a region of a vessel in a body comprising a stent portion and an actuator portion and methods for the use and manufacture thereof. The stent portion is comprised of an elongate perfusable vessel supporting portion adapted to be configurable between a reduced size for placement in the vessel and removal therefrom and an expanded size for structurally supporting the vessel. The stent portion also includes perfusable end portions connected to and forming ends of the vessel supporting portion and adapted to allow fluid flow therethrough. The actuator portion includes a proximal end extending out of the body and a distal end connected to the stent portion and operable by manipulation at the proximal end thereof to configure the support portion into a reduced size and an expanded size.

With this arrangement, the temporary stent may be positioned in the desired region in its contracted form and then expanded to provide the desired support to the vessel. The temporary stent may be left in place for a selected period of time and then be easily removed by the physician. Significantly, the arrangement of the present invention allows the stent to remain in place without significantly interfering with the flow of fluids through the vessel.

In one preferred arrangement, the stent is attached to the distal end of a flexible catheter and a fluid conduit is provided which extends from the proximal end of the catheter to a point close to the stent. This fluid conduit provides a channel through which medicine may be introduced to an area near to the stent. Angiographic fluids, such as dyes, injected into the blood flow in the vessel allow imaging of the vessel and blood as it passes through the stent.

BRIEF DESCRIPTION OF THE FIGURES

FIG. 1 depicts a first preferred embodiment of the present invention.

FIG. 2 shows a distal portion of the embodiment depicted in FIG. 1 with the stent portion in a reduced contracted configuration.

FIG. 3 shows a distal portion of the embodiment depicted in FIG. 1 with the stent portion in an expanded configuration.

FIG. 4 is a longitudinal sectional view showing a portion of the embodiment depicted in FIG. 1.

FIG. 5 is a longitudinal sectional view showing a portion of the embodiment depicted in FIG. 1.

FIG. 6 depicts a distal portion of another embodiment of the present invention.

FIG. 7 depicts a distal portion of another embodiment of the present invention in a contracted configuration.

FIG. 8 depicts the distal portion of the embodiment shown in FIG. 7 in an expanded configuration.

FIG. 10 is a cross section of an embodiment of a wire component along lines 10—10' of FIG. 2.

DETAILED DESCRIPTION OF THE PRESENTLY PREFERRED EMBODIMENTS

Figure 9:
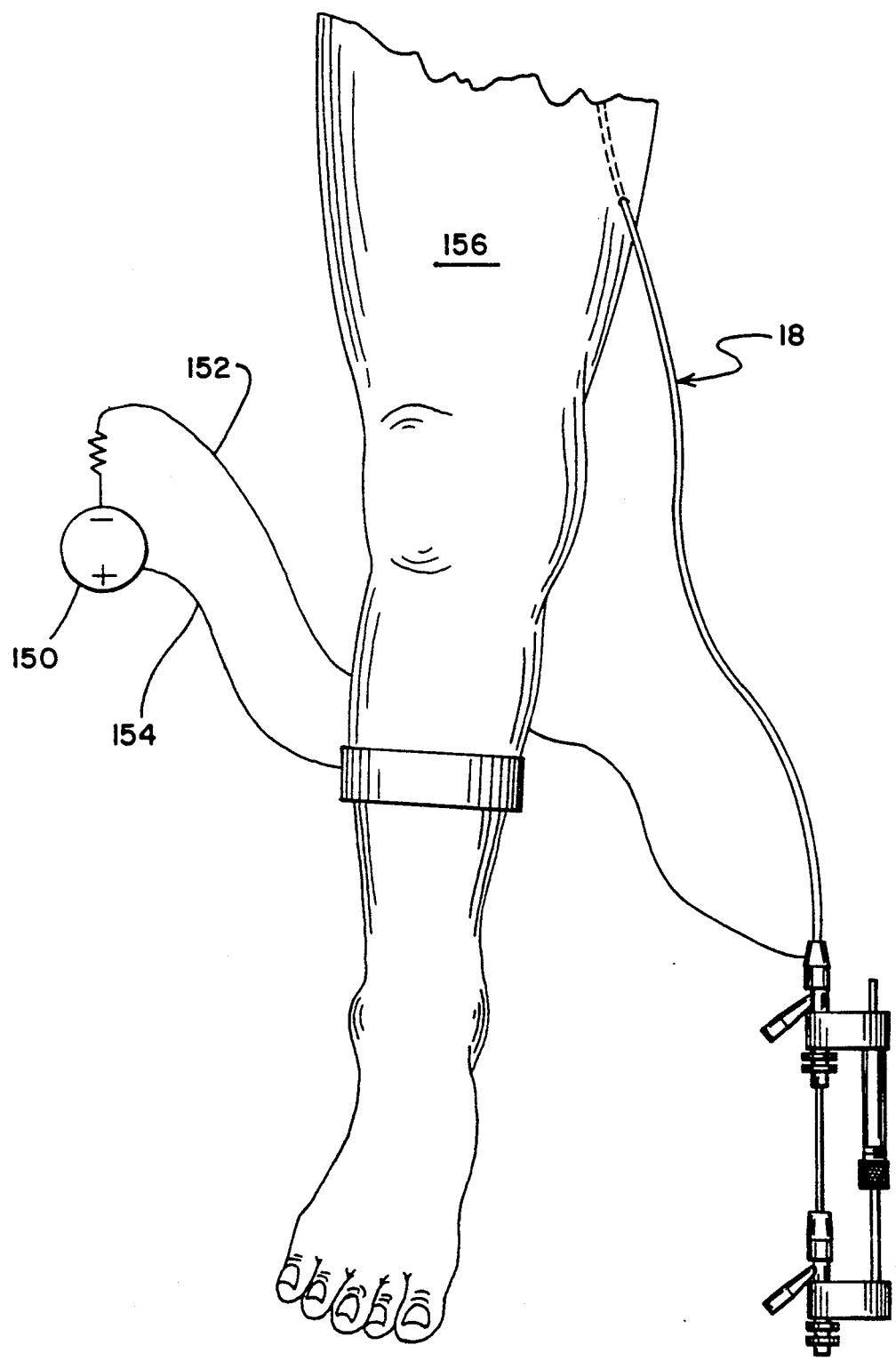
FIG. 9 depicts another embodiment of the present invention.

Referring to FIG. 1, there is depicted a first embodiment of the present invention. The embodiment of FIG. 1 is a temporary stent 10 which can be placed in the vascular system of a patient after a procedure such as angioplasty, atherectomy or other interventional therapies. Although the temporary stent 10 is particularly useful in procedures involving blood vessels, it may be used in other fluid carrying vessels in the patient's body.

As used herein, the term "vascular system" refers to a vessel for conveying body fluids. The temporary stent 10 is intended for placement in a vascular system for limited durations of time from several minutes to up to several days.

In the embodiment of the invention depicted in FIG. 1, the temporary stent 10 includes a perfusable stent portion 14 and an actuator portion 18. The stent portion 14 is connected to a distal end 20 of the actuator portion 18. When the temporary stent 10 is being used in a patient, the actuator portion 18 extends proximally from its connection to the stent portion 14 through the vascular system and out of the body of the patient. The proximal end 22 of the actuator portion 18 which extends out the body of the patient is connected to one or more and preferably two manifolds 24 and 26.

The stent portion 14 is expandable and contractable so that it can be positioned in the vascular system at the specific location where needed and then expanded to an appropriate size (i.e. approximately the same diameter as the vessel in the region where placed) thus supporting that vascular region. When in its expanded configuration, the stent portion 14 provides support to the vascular walls thereby preventing constriction of the vascular region in which it is located and maintaining the vascular lumen open.

The construction and materials for the stent portion 14 should provide that the stent be perfusable, i.e. it should allow blood flow therethrough both in the axial direction of the vessel to maintain blood flow through the region in which the stent is located as well as in the radial direction so that any vessels that branch off from the region of the vessel into which the stent portion is placed will not be occluded. Thus, the stent portion 14 should be relatively transparent to blood flow in order to maintain vascular function while at the same time providing support for the vessel walls in the region where it is located.

Expansion and contraction of the stent portion 14 inside the patient's body may be accomplished from outside of the patient's body by means of manipulation of the actuator portion 18 from the proximal end 22 thereof which is located outside the patient's body. In this embodiment, the actuator portion 18 comprises a first elongate member 28 that connects to a proximal end 30 of the stent portion 14 and a second elongate member 32 that connects to the distal end 34 of the stent portion 14. Relative movement of the first elongate member 28 and the second elongate member 32 causes expansion and contraction of the stent portion 14, as explained in more detail below. The distal end 20 of the actuator portion 18 remains in place in the body during the period of time that the stent portion 14 is in place in the vascular system and during this time the proximal end 22 of the actuator portion 18 extends out of the patient's body. At the proximal end of the actuator portion 18, the first elongate member 28 terminates at a manifold 24 and the second elongate member 32 terminates at the manifold 26. In a preferred embodiment, these manifolds include hemostatic valves and Y-connecters for administering fluids, such as medicines through these manifolds, as described below.

In a preferred embodiment, the stent portion 14 is comprised of a braid made of a plurality of helically wound wires forming an elongated hollow tube. Typically, half of the wires forming this tube will be wound in one helical direction and the other half will be wound in the opposite helical direction and interwoven with the first half. Braiding of these wires provides for an elongated, expandable hollow tube that can, in a preferred embodiment, increase in diameter when the ends of the hollow tube are moved closer relative to each other and decrease in diameter when the ends of the hollow tube are move apart relative to each other. The ratio by which the stent portion expands depends upon the spacing between adjacent wires that make up the braid as well as the cross sectional dimensions of each of the individual wires.

The stent portion 14 may be provided in a wide range of sizes and stiffnesses to meet the requirements for use with different lesions or flaps in a patient's vascular system. The stent portion 14 is constructed to be flexible enough to traverse its way to the region of the vascular system where it is to be located and expanded to provide support for the region of the vascular system, such as the site of previous angioplasty or other treatment.

The stent portion 14 terminates in a distal end 34. Located inside the hollow tube of the stent portion 14 is the second (or inner) elongate member 32. The second elongate member 32 is connected to the distal end 34 of the stent portion 14, as explained below. The second elongate member 32 extends proximally from its connection to the distal end 34 of the stent portion 14, through the hollow tube of the stent portion 14, and through an inner lumen of the first elongate member 28 to the proximal end thereof. In accordance with this embodiment, relative movement between the first elongate member 28 and the second elongate member 32 causes corresponding movement of the proximal end 30 and distal end 34 of the stent portion 14 thus in turn causing expansion or contraction of the diameter of the elongate hollow tube of the stent portion 14.

In FIG. 2, the temporary stent 10 is depicted in its constricted configuration with the elongate hollow tube of the stent portion 14 having a reduced diameter. In this configuration, the second elongate member 32 extends distally from the first elongate member 28 so that the length of the stent portion 14 is L1. In FIG. 3, the second elongate member 32 is positioned at a location more proximate relative to the first elongate member 28 than in FIG. 2 (i.e., in the direction of arrow 35) causing the length of the stent portion 14 to be equal to L2 (L2 being less than L1). In the process of moving proximally relative to the first elongate member 28, the second elongate member 32 causes the proximal and distal ends 30 and 34, respectively, of the stent portion 14 to move relatively closer together thus causing the diameter of the elongate hollow tube of the stent portion 14 to expand to a dimension suitable for supporting a region of the vascular system. The temporary stent 10 can be maintained in this expanded configuration by fixing the proximal ends of the first and second elongate members 28 and 32 for the duration of the time that the temporary stent 10 is maintained in the vascular system. This may be done by attaching a clamp 39 or similar device to the proximal ends of the first elongate member 28 and the second elongate member 32 at the manifolds 24 and 26. These two elongate members can be later disengaged from each other to permit reducing the diameter of the temporary stent 10 for removal thereof from the body.

In order to provide a means by which the position of the temporary stent 10 in the body of the patient can be determined, one or more radiopaque markers, e.g. 40 and 41 may be located on a distal region of the stent, for example on a distal region of the second elongate member 32. These markers may be bands of radiopaque materials such as platinum, tantalum, gold, tungsten or a tungsten-iridium alloy.

Referring to FIG. 4, there is depicted a longitudinal cross section of the distal end of the second elongate member 32. In this embodiment, the second elongate member 32 is an inner catheter 44. As depicted in FIG. 2, the distal end 34 of the stent portion 14 surrounds an outside wall of the inner catheter 44. A collar 46 surrounds and affixes the distal ends of the wires that make up the braid of the stent portion 14 to the distal end of the inner catheter 44 (i.e. first elongate member 32). The collar 46 may be made of a balloon tubing polyolefin or other ultra-thin wall polymers. The collar 46 may be heated to fuse to the outer wall of the inner catheter 44 or connected thereto by an adhesive or other suitable means. In this manner, the distal end 34 of the stent portion 14 may be securely fixed to the inner catheter 44 suitably for the duration of the use of the temporary stent 10. A distal tip 48 of the temporary stent 10 is formed of an extension of the inner catheter 44 distally past the collar 46. This extension may be approximately 0.25 cm. The inner catheter 44 has a lumen 50 therewithin that communicates with an opening 52 at the distal tip 48.

Referring to FIG. 5, there is a longitudinal sectional view depicting a portion of the proximal end 30 of the stent portion 14 and the actuator portion 18 and specifically the connection of the proximal end 30 of the stent portion 14 to the first elongate member 28 of the actuator portion 18. In this embodiment, the first elongate member 28 is an outer catheter 54. As shown in FIG. 5, the outer catheter 54 includes an inner tubular layer 56 and an outer tubular layer 58 that is concentric with the inner tubular layer 56. The outer diameter of the outer catheter 54 would be approximately close to, but may be slightly larger than, the contracted diameter of the stent portion 14. Thus, for coronary applications, the outer catheter 54 may be approximately 1.35 mm, and for peripheral applications the outer catheter 54 may have a diameter of approximately 2.10 mm. The length of the outer catheter 54 could be made to various sizes to be suitable for different treatment sites. For coronary applications, the length of the outer catheter 54 would be approximately 175 cm, for example.

In this embodiment, the proximal end 30 of the stent portion 14 is secured between the inner and outer concentric tubular layers 56 and 58 by extending the wires of the braid proximally between these concentric layers. The concentric tubular layers 56 and 58 and the wires of the braid of the stent portion 14 may be bonded together by an appropriate adhesive or by heating. A frictional fit may also be suitable. Preferably, the wires of the braid extend the entire length proximally to the proximal end of the first elongate member 28. Alternatively, the wires of the braid of the stent portion 14 may extend only a short distance or an intermediate distance proximally between the concentric tubular layers 56 and 58.

In the preferred embodiment, the inner tubular layer 56 terminates a distance proximally from the distal end of the outer tubular layer 58. This enables the outer catheter 54 (i.e., first elongate member 18) to be reduced in diameter in the distal region thereof forming a necked down portion 60 to facilitate positioning the temporary stent 10 in a region of the vascular system. The necked down portion 60 of the outer catheter 54 may be approximately 3 to 30 cm in length.

Referring again to FIG. 3, when the stent portion is in its expanded configuration, the proximal 30 and distal 34 ends of the stent portion 14 will assume a proximal and distal truncated conical profile regions 62 and 64. These truncated conical profile regions 62 and 64 taper from a narrow dimension where the wire braid is affixed to the actuator portion 18 proximally and distally (i.e., first and second elongate members 28 and 32) up to the expanded diameter of the stent portion 14. These regions 62 and 64 may be linearly tapered, but a non-linear taper may also be provided. The type of taper depends upon the type of braiding method used. Because the diameter of the second elongate member 32 is less than the diameter of the first elongate member 18, the distal tapered region 64 may not correspond exactly in size or slope to the proximal tapered region 62. In both the proximal tapered region 62 and the distal tapered region 64, the braiding method used preferably provides for relatively large distances between adjacent wires to provide correspondingly large openings around and through the plurality of wires at the ends of the stent portion 14 to facilitate blood flow therethrough.

In this embodiment, the temporary stent 10 may be positioned in the vascular region over a guidewire 70 through the lumen 50 of the inner catheter 44. The guidewire 70 may be a standard guidewire suitable for the region of the vascular system into which the stent will be located. According to this embodiment, the guidewire 70 is positioned in the vascular system across the region where it is desired to install the temporary stent 10. The guidewire 70 may be positioned by standard procedures. The diameter of the lumen 50 of the inner catheter 44 is of a sufficient size to allow the stent portion 14 to be advanced in the vascular system over the guidewire 70. The temporary stent 10 including the stent portion 14 and the distal end of the actuator portion 18 is advanced over the guidewire 70. The lumen 50 of the inner catheter may be compatible with 0.014, 0.016, or 0.018 guidewires for coronary applications and with up to 0.038 guidewires for peripheral applications.

Alternatively, the temporary stent 10 could be located in the vascular region by guiding it through a separate catheter (e.g. a delivery catheter) large enough to contain the temporary stent 10 in its contracted configuration.

For coronary applications, the stent portion 14 of this embodiment is expandable from a size of approximately 1.25 mm or less to up to approximately 4.0 mm. When used for peripheral applications, the stent portion 14 of the temporary stent 10 may have a contracted diameter of less than approximately 2.0 mm and an expanded diameter of up to approximately 6.0 mm. The length of the stent portion 14 is approximately 2.5 to 5 cm when in its most extended position (i.e. when the diameter of the stent portion 14 is in its contracted configuration). When the diameter of the stent portion is in its expanded configuration, the length of the stent portion is somewhat less, e.g. approximately 1.5 to 3.5 cm.

In this embodiment, fluids such as medicines may be introduced to the vascular system via the lumen 50 of the inner catheter 44 as well as through a lumen 72 of the outer catheter 54 around the inner catheter 44. Medicines introduced via the inner catheter 44 will enter the vascular system at the distal end 48 of the stent portion 14 via opening 52. In this embodiment, sufficient space is provided in the lumen 72 of the outer catheter 54 around the inner catheter 44, so that a second passageway for the introduction of fluids such as medicines to the vascular system is also provided. Medicines introduced via the lumen 72 of the outer catheter 54 will enter the vascular system at the proximal end 30 of the stent portion 14. In this manner, the attending physician has the choice of selecting the point of entry for medicines administered e.g., either upstream or downstream of the stent portion 14. For instance, medicines, such as non-thrombogenic drugs, can be administered upstream of the stent portion 14 where they would be most effective in the region of the stent portion 14.

To remove the temporary stent 10, the stent portion 14 is first contracted from its expanded configuration to a reduced configuration. To do this, the first elongate member 28 is moved proximally relative to the second elongate member 32 thereby drawing down the diameter of the stent portion 14 to a size to facilitate removal from the vascular system. The wires of the stent portion 14 should smoothly peel from the vessel wall causing no or only minimal trauma. It is not necessary that the stent portion 14 be drawn down entirely to its completely reduced size. It is sufficient that the stent portion 14 is drawn down sufficiently to disengage the inner walls of the vascular region and to be of a size sufficiently small to traverse the vascular system out of the body. Then, after the stent portion 14 is in a reduced configuration it may be removed from the vascular system by drawing it out by means of the attached actuator portion 18.

In the first presently preferred embodiment of the present invention, the inner catheter 44 is comprised of a 0.021×0.028 inch polymeric tubing. The tubing used may be a blended Poly-Ethylene comprised of High Density Polyethylene (HDPE) and Low Density Poly-Ethylene (LDPE). Alternatively, the inner catheter 44 may also be constructed of Poly-Propylene, TPFE teflon or TPX. (TPX is a trade name for the Methyl Methylpentene Copolymer manufactured by Mitsui Plastics, Inc. and distributed from White Plains, N.Y.). The use of TPX enables the stent to be used for ultrasound imaging of the vessel that is being supported by the stent because the acoustical properties of this polymer match to that of water and blood.

Referring to the first elongate member 28, the inner tubular layer 56 may be constructed of the same combination of polymers described for the inner catheter 44. The inner tubular layer 56 may terminate 3 to 30 cm proximally from the proximal end 30 of the stent portion 14. This provides for the ability to reduce the section of the outer layer 58 by way of a drawing (or necking operation) on the outer layer 58. The preferred size for this inner tubular layer 56 of the first elongate member 28 is 0.033×0.039 inch.

The outer tubular layer 58 of the first elongate member 28 may also be constructed of blended HDPE-LDPE, or polypropylene. The dimensions of the outer tubular layer 58 of the preferred embodiment may be 0.045×0.053 inches in the proximal section of the first elongate member 28 extending from the manifold 24 at the proximal end to approximately 3 to 30 cm from the proximal portion 30 of the stent portion 14. From this point distally, the outer tubular layer 58 may be preferable reduced to 0.039×0.045. This may be accomplished by a necking or drawing operation which is achieved by pulling the tube through a heated die and allowing the plastic to reflow.

The inner dimension of the outer tubular layer 58 as well as the distal necked region 60 is adjusted accordingly for a 3.0 or 3.5 mm stent as may be seen to accommodate the wire of greater thickness. Since the outer diameter of the inner tubular layer 58 is 0.039 inches the placement of the braid on top of this layer, i.e. in the lumen 72, adds a factor of four times the wire thickness to the profile of the device prior to installation of the outer tubular layer 58. It is therefore apparent that the inner diameter of the outer tubular layer 58 should be adjusted to a minimum of 0.047 inches for the 3.0 mm and 3.5 mm versions. The tubing dimension may then be adjusted for the outer tubular layer to 0.055.

When devices are designed for use within the coronary arterial system size becomes a very significant factor. Each 1/1000th of an inch is significant both because of the primary concern which is restriction of flow, but also because of the added stiffness that results when a composite of tubular layers are sandwiched together to form the actuator member. For this reason, in the preferred embodiment, wire of rectangular cross section (herein referred to as flat wire) is utilized. The preferable size wire to make a 2.0 mm stent is 0.003 inches. For a 2.5 mm stent, wire of a size of 0.003 to 0.0035 may be used. For a 3.0 and 3.5 mm stent, wire of either 0.0035 or 0.0040 should be used. From this, the advantage of using flat wire becomes apparent. For each of the stent sizes, added thickness due to the braid is detailed below.

| SIZE | WIRE SIZE | STACK UP HEIGHT DIAMETRAL |
|---|---|---|
| 2.0 | .0015 FLAT | .006 |
| 2.0 | .003 ROUND | .012 |
| 2.5 | .0015 FLAT | .006 |
| 2.5 | .003 ROUND | .012 |
|  | .0035 ROUND | .014 |
| 3.0 | .002 FLAT | .008 |
| 3.0 | .0035 ROUND | .014 |
|  | .004 ROUND | .016 |
| 3.5 | .002 FLAT | .008 |
| 3.5 | .0035 ROUND | .012 |
| 3.5 | .004 ROUND | .016 |

From the above, the significance of the use of flat wire can be appreciated. It may be seen that a large profile change results using flat wire as opposed to round wire. Additionally, the use of the larger flat wire results in devices that are considerably stiffer.

In the preferred embodiment, the braiding operation uses flat wire. In the preferred embodiment, a 2.0 mm stent is constructed with a braid mesh network using stainless steel wire of rectangular cross section with a thickness of 0.001 inch × 0.004 inch. In the preferred embodiment, for a 2.5 mm stent the wire used is stainless steel wire with a rectangular cross section of 0.0015 inches in thickness and 0.004 inch in width. In the preferred embodiment, the 3 mm stent is constructed with a stainless steel wire of rectangular cross section with 0.002 inch thickness and 0.004 inch width. A 3.5 mm stent is constructed with either a 0.002 inch thickness and 0.004 inch width, or a 0.002 inch thickness and 0.005 inch to 0.007 inch width.

The wires that are used for the braid of the stent portion can be fragile due to their small size and care should be exercised in the manufacturing process. This is particularly true for the smaller wires such as the 0.003 inch round or the 0.0008 to 0.0015 thickness flat wires.

In the preferred embodiment, the wire used in each of the aforementioned braiding operations is 304 stainless steel in a spring temper. The specific wire used is the Hyten (TM) wire available from Fort Wayne Metals of Fort Wayne, Ind. Additionally, any one or more or and preferably 2, 3, or 4 of the 8 wires that comprise the braid may be made of an alloy of 92% platinum and 8% tungsten for the purpose of providing radiopacity. These alloys are commercially available from a number of sources, such as Sigmund Cohn Corp. of Mount Vernon, N.Y., or California Fine Wire of Grover City, Calif.

The braiding process of the present invention requires modification of a commercially available braiding machine to achieve the desired consistency and braid density. In the preferred embodiment, for both the round and the flat wires, the braid pattern is composed of 8 wires. Braiding machines range in size from 16 carriers to 100 carriers. The braiding machine used for the manufacture of the stent described herein is a modified KoKobun SL-4-16 braider available from Wardwell Braiding Machine Co. of Rhode Island, N.Y. This same company also manufacturers a series of braiders under the New England Butt trade name. The braiders may be manufactured to accommodate 4, 6, 8, 10, 12, 16, or 24 bobbins in the machine groups defined as NE Butt #1, #2, or the B-11-8. These are all very small bench top versions that are used for small fibers or wire when fragile tensioning is required. The KoKobun is similar to the New England #2. The N E Butt B-9 which is a New England Butt #1 could conceivably be modified to make a 6 or a 5 wire braid which may also be used for this application.

Machine modifications include the removal of 8 of the 16 carriages, as well as the installation of ultra light tensioning springs on the braider carriages. Additionally the tent angle (i.e. the angle with which the wires approach the central core on which the braid is being installed) normally is free to float up and down as the braiding wire position and rate equilibrate on the central core. For the application of flat wire, the wire may tend to get caught on other wires which are being applied in the opposing direction. The wires then would get flipped over every few linear inches of braid therefore making the segment unusable or incorporatable within the catheter. This problem may be eliminated by providing an angled guide made of a low friction material such as teflon and containing the angle for which the desired tent angle should be guided.

The size and density of the stent is controlled by three variables: the size of the central core to which the braid is being applied; the rate of advancement of the central core through the braid region; and the angular velocity of the braiding carriages. These variables relative to each other determine the "pick" (number of wire group intersections per inch) density of the braid pattern. These variables also determine the size of the stent that will be manufactured.

In the preferred embodiment, a 2.0 mm stent is made on a central core with a size of 0.050 inches and a density of 10 per inch. When removed from the core the stent will spring from the I.D. of 0.055 to 2.0 mm and have a pick density of approximately of 7 to 15 per inch or approximately 0.14 to 0.07 inches between groups or 3.6 mm to 1.8 mm. The degree for which the stent expands when removed from the core depends on the pick density during the braiding operation.

The table below outlines the preferred expanded pick densities for the individual stent configurations. The braiding machine used must be modified so that the take up velocity of the central core and the radial velocity may be adjusted very precisely to achieve the exact density required. Due to the addition of the guide, as explained above, the density of the braid will not be allowed to assume its own pattern density by climbing up and down the central core, but instead will assume the required density.

| size | core size | pic distance when expanded |
| --- | --- | --- |
| 2.0 | .050 | 1.8 to 3.6 mm |
| 2.5 | .055 | 1.8 to 3.6 mm |
| 3.0 | .062 | 1.8 to 3.6 mm |
| 03.5 | .068 | 1.8 to 3.6 mm |

From the table, the desired density in this preferred embodiment is obtained by placing the bridges 1.8 to 3.6 mm apart. As mentioned above and unlike a dilation device, a feature of the temporary stent is that it is highly perfusable. This is accomplished in part by minimizing the density of metal within the vessel which may restrict the blood flow both though the ends of the stent and also radially from the sides of the stent. This is important because frequently side branches to the blood vessel are contained in the stent region and flow must exit the stent to keep these side branches perfused. The area or size of the stent should be minimized to maximize perfusion while maintaining sufficient structural support for a flap or other damaged part of the vessel.

The stent portion should not only be perfusable to allow blood flow therethrough, but should also minimize surfaces upon which a thrombus might form. The vascular system is very active with respect to clot formation once a vessel has been damaged or subjected to other trauma such as during an angioplasty. Any device that is installed for more than a few minutes is susceptible to clot formation. Because in some embodiments, the temporary stent may be used for up to several days, it should also provide for minimization of clot formation.

One way the temporary stent minimizes clot formation is by preparation of the surfaces of the wires of the stent portion. The wires of the braid in the preferred embodiment are made of rectangular wires braided into a 4, or 8 wire braid and rectangular wire may, by reason of the manufacturing processes, have edges that are very sharp. The wire is made by initially drawing it through a die in order to form the specific size that is desired. During this process the temper of the spring may be modified by the cold work that is being induced into the wire from the forceful shaping of the wire. In the case of the HyTen 304 SS wire, the spring tempers are being achieved with pressures which are substantially greater than 300,000 psi. This spring temper is very desirable from the standpoint of imparting desirable properties to the stent. Specifically, the stent must be resilient to return from its initial contracted configuration to the full expanded state with only a minimal application of external force. The temper is relevant to the fabrication process and ultimately to the product performance.

The edges formed on the flat wire are rounded off. The preferred method used to radius the corners of the flat wire is electropolishing which removes edges or protrusions of the material and passivates the metal without altering the bulk properties of the metal. The metal is left in a passive state by the electropolishing process and the metal is also highly resistant to corrosion.

The electropolishing operation requires the use of an electrolytic fluid. This fluid must dissolve the products formed on the work piece which in this case is the metal stent surface by electro-chemical action. High current densities of 1000–5000 amps per square inch are maintained between the workpiece and a cathode. A DC power supply is used to provide the required power. The rate of removal is regulated by the current flow through the work piece. Corners or asperities extending from the surface of the work piece have a greater projected surface area/volume ratio than does the flat area. For this reason, material is removed from such regions at an accelerated rate. Further, this operation is ideal for smoothing the flat wire in the stent region and radiusing the corners which otherwise would exhibit sufficient sharpness to potentially scrape the endothelial cells from the inside of the vessel thus promoting thrombus. After electropolishing, a flat wire 79 may possess a rounded cornered cross sectional profile, as depicted in FIG. 10.

The electropolishing operation may be performed as follows. The electropolishing solution should be selected which meets the operational requirements. An acidic solution should be selected which is compatible with the electro-chemical characteristics such that material may be removed without the production of carbides or other metal impurities on the surface which will result in corrosion. A direct current (DC) power supply is provided to provide the electromotive potential required to force the electrochemical sacrifice of metal from the surface. The positive (+) terminal (the anode) is attached to the workpiece, and the negative terminal is attached to a non-corrosive negative (−) terminal piece (the cathode).

The stainless steel wire requires a voltage of approximately 5 volts to perform the polishing operation. This voltage is dependent on the electropolishing solution being used as the electrolyte. The solution being used in the preferred embodiment is a solution of phosphoric acid, citric acid, deionized water, and ethyl alcohol. The operation is performed at an elevated temperature in order to increase the rate of metal removal and provide for the smoothest possible surface. Other electrolytes are available additionally that are effective on the stainless steel. These solutions are frequently combinations of alcohol, multiple acids, and water. Sulfuric acid based solutions are frequently used in electropolishing of stainless steel. If other metals are used in whole or in part in the braid, e.g. platinum or tungsten, in order to provide for radiopacity, modifications to the method may be appropriate. Electropolishing solutions used on the platinum-tungsten material used on the rectangular wire used in the braid may be polished using a HF acid solution in the same manner as described above, or may be mechanically radiused prior to incorporation in the braid by winding the wire from spool to spool and passing over a sequence of polishing wheels. This may be preferred to avoid dealing with HF acid. Many of the other metals which alternatively will provide opacity under X-ray also are quite noble and require HF acid for polishing. The mechanical polishing method is preferable for these metals.

The ease of electropolishing the stainless steel and the smooth, burr-free surface that is provided makes this the preferred method over mechanical removal. It must be understood that mechanical removal is also possible and relatively easy with the stainless steel.

The stainless steel that is in the austenite alloys provides a self-repairing oxide film which prevents corrosion. Passivity may be diminished or lost by any process in which a localized oxygen withdrawal occurs by any means. Heating or chemical reactions are capable of relieving this oxygen. The passive state may be restored to the material by exposing the material to an oxidizing environment such as nitric acid. The passivation state may be altered during the electropolishing operation if the parameters are not closely controlled. The voltage driving the chemical reaction will affect the passive state of the remaining surface. In the case of the preferred process utilizing the phosphoric acid solution the voltage and temperature at which the process is operated at is 80 degrees celsius and $5 +/- 0.25$ volts. The specific solution composition is 757.6 cc/liter phosphoric acid, 181.8 cc/liter de-ionized water, 60.6 cc/liter denatured alcohol, and 303.0 grams/liter citric acid.

In addition to the electropolishing step described above, clot formation can further be minimized by the application of one or more antithrombogenic coatings. In the preferred embodiment, the braided wires are coated in two layers with a silicone oil solution. The surface is treated twice to achieve complete surface coverage. Since the engagement of the braided stent section results in a relative movement of the individual wires with respect to each other, the stent region is coated in both an expanded and contracted configuration. The coating used in the preferred embodiment is Dow Corning (R) MDX4-4159 silicone fluid. The coating may be applied in accordance with the instructions in Dow Corning Bulletin 51-599 (July 1982) for the MDX4-4159 silicone fluid which is incorporated herein by reference.

Although a braid is a presently preferred construction for the perfusable stent portion 14, other alternative embodiments may include a plurality of parallel wires forming a hollow cylindrical tube each wire substantially parallel to the axis of the hollow cylindrical tube. In this alternative construction, at the ends of the elongate hollow tube formed by the plurality of wires, each wire would include an oblique bend so that each wire could be connected to the actuator portion which is aligned with the axis of the hollow tube formed by the wires. Relative displacement between the ends of the wires would cause the oblique angles at the end of each wire to change thereby increasing or decreasing the diameter of the hollow tube to enable placement or removal of the stent from the vascular region of the patient's body. Other alternative constructions for the stent portion may also be provided.

In accordance with the present embodiment, it is presently preferred to utilize a temporary stent of a specific and selected expanded size suitable for the region of the vascular system in which it is intended to be installed. Accordingly, it is presently intended with this embodiment to utilize different sizes of stents where different expanded sizes are needed. Alternatively, where there is a need to apply a temporary stent in a small size vessel, instead of using a small size temporary stent, it is possible to utilize a large size temporary stent (i.e. one that is expandable to a large diameter) but to only expand it partially to an intermediate expanded diameter size. This could be accomplished by fixing the proximal ends of the actuator portion 18 and the inner elongate member 26 at an intermediate position between where the catheter is fully compressed and where it is fully expanded.

These dimensions provided above are intended as approximate and other sizes and dimensions may be selected and designed in accordance with the teachings of the present invention.

Referring to FIG. 6, there is depicted the distal end of another embodiment of the present invention. The proximal end (not shown) could function similarly as in the first described embodiment. In this embodiment, a temporary stent 80 has a stent portion 82 and a actuator portion 84. The stent portion 82 is connected to the actuator portion 84 at a proximal end 86 of the stent portion 82. An inner elongate member 88 extends through the stent portion 82 and the actuator portion 84. As in the previous embodiment the inner elongate member 88 is connected to a distal end 90 of the stent portion 82. Also, as in the previous embodiment, the inner elongate member 88 may be moved relative to the actuator portion 84 to cause expansion and contraction of the stent portion 82.

In this embodiment, the inner elongate member 88 further includes a guidewire tip 92 that extends distally from the distal end 90 of the stent portion 82. The guide wire tip 92 is flexible and formable and includes a rounded portion 94. The guidewire tip 92 facilitates positioning the temporary stent 80 in the vascular system. In FIG. 4, the guidewire tip 92 is depicted having a curvature although it should be understood that the guidewire would normally be provided in a straightened position and that the curvature may be imparted by a physician prior to insertion into the vascular system of the patient in order to facilitate positioning of the stent. The guidewire tip 92 may assume a curvature such as depicted during its positioning in a tortuous vessel path. In this embodiment, the temporary stent 80 may be positioned by means of the guidewire tip 92 instead of over a separate guidewire that is located the inside an inner catheter (e.g. lumen 50 of inner catheter 44 in the first embodiment).

Referring to FIGS. 7 and 8, there is depicted another embodiment of the present invention. In FIGS. 7 and 8, a temporary stent 100 includes a stent portion 102 and an actuator portion 104 connected to each other at a proximal end 106 of the stent portion 102. In this embodiment, a distal end 108 of the stent portion 102 includes a cylindrical shaft 110 having a cylindrical opening 112 therethrough. The cylindrical shaft 110 includes at least one bearing surface 116 thereupon. An inner elongate number 118 is located in the hollow tube of the formed by the stent portion 102 and extends proximally as in the previous embodiments. Unlike the previous embodiments, the inner elongate member 118 is not fixed to stent portion 102. Instead, the inner elongate portion 118 has a narrow distal portion 120 positioned to be slidingly received in the opening 112 of the shaft 110. A first shoulder 122 on the inner elongate member 118 is located to bear upon the surface 116 when the inner elongate member 118 is moved distally. The inner elongate member 118 also includes a second shoulder 126 formed distally of the narrow distal section 120. The second shoulder 126 is located to bear upon another surface 128 of the inner elongate member 118. Proximal movement of the inner elongate member 118 causes the shoulder 126 to bear upon the surface 128 causing expansion of the stent portion 102. As shown in FIG. 8, the second shoulder 126 may form part of a guide wire tip 130. However, other configurations for the tip are also suitable. With the embodiment of the invention depicted in FIGS. 7 and 8, limited axial movement of the inner elongate member 118 is provided which may be suitable and desirable for positioning and removal of the removable stent. As shown in FIGS. 7 and 8, the surfaces 116 and 128 and the shoulders 122 and 126 may be formed to prevent removal of the inner elongate member 118 from the actuator portion 104 and stent portion 102 although removability may be provided by alignment of the shoulders 106 with the bearing surface 128. As in the previously described embodiment, with this embodiment a separate guide wire is not required to position the temporary stent inside the vascular system.

As described above, because the temporary stent will be left in the vascular system for a period of time, the temporary stent should avoid or minimize clotting or platelet aggregation in and around the stent portion. Also, it is advantageous to reduce the tendency of the stent to permanently adhere to the inner surface of the vascular walls in order to facilitate removal of the stent. This may be accomplished by providing or imparting to the temporary stent properties that will minimize these tendencies.

In one alternative embodiment, the stent portion includes a coating of a slow release polymer having antithrombogenic properties. Such polymers include drugs such as urokinase, heparin, antithrombin III or other thrombon-resistive agents. The polymer used may be polyethylene or a polyolefin.

The natural surface charge that is present intrinsically on a material is considered to be a factor in the chain of successive events that results in the formation of mural thrombus on an artificial surface. Although, the blood coagulation cascade is complex and not fully understood, it is accepted that on an artificial surface, characteristics such as low surface energy (i.e. hydrophobic), and the electro-negativity of the surface affect the initial events that are important to subsequent reactions or events that result in the formation of thrombus. For this reason, in the preferred embodiment, the surface is coated with a silicone oil solution which is of a low surface energy. Other alternative coatings that will provide relative thromboresistance include teflon, and pyrolytic carbon. While pyrolytic carbon has a relatively high surface energy of approximately 50 dyne/cm which is generally not considered thromboresistant, upon exposure to blood it has been observed to present a change to about 30 dyne/cm. This is considered to be thromboresistant and is thus a widely used material in coating of metal heart valves. The relative success of the stent in placement in vivo is dependent upon the ability to manipulate the surface characteristics to "tune" the device to the requirements that are present but not fully understood in the blood chemistry reactions.

Other methods may be used to provide this property. For example, the surface of the stent portion may effectively be charged and polarized to prevent the sequence of events that results in clot formation. By installing an external ground plane to the patient and placing a lead to the metal surface, the braid may be energized such that it is essentially an insulated capacitor which will provide the surface charge of desired magnitude, and polarity. The voltage level supplied to the wire is effectively additive to the natural negativity of the surface. The net potential may be effectively adjusted to a zero, positive, or negative charge. Referring to FIG. 9, a charge is imparted to the stent portion. The DC power supply 150 is located outside the vascular system. Only a small current is necessary (for example, less than 50 microamps). This could be provided by a small battery such as a watch battery. This would be sufficient to impart a charge to the stent portion to minimize the tendency for clotting materials to form on the stent portion. The polarity may be selected based upon consideration of factors, such as material, coating, medication, etc. A lead 152 is connected to the stent portion of the temporary stent and the other lead 154 is connected to the body 156 of the patient. As described above, the proximal end of the stainless steel braid comprising the stent portion could extend all the way to the proximal end of the outer catheter to form part of, or to connect to, lead 152. The braid may provide a pathway proximally to the manifold which provides an electrically conductive pathway so that a surface charge may be placed which in effect overrides the natural electronegative characteristics of the stainless steel metal surface from which the braid is formed. Alternatively, the wires that make up the stent portion may connect to a lead at a point proximally from the proximal end of the stent portion and the lead could extend proximally.

Additionally by providing a waveform polarizing function, the stent surface may be polarized with a time varying potential. The application of a high frequency current in the kilohertz to the megahertz range is a procedure that has been tested for healing of wounds. The construction of the stent portion is designed to have a periodic surface contact with the wounded vessel, and a network for applying desired voltage, and polarities and frequencies to an intimate contact with the wounded vessel. The device may be constructed to apply current to the stent of 0 to 20 micro amp to the surface when an uncoated surface is used or when a noble coating such as gold or platinum is applied. Gold may be applied by standard vapor deposition process known as sputter coating, or by an electro-chemical plating process. Platinum is normally electro-plated.

Another method for imparting a charge to the stent portion is by means of an RF signal. By this method, the proximal end of the stent portion will be connected to a RF source.

It is intended that the foregoing detailed description be regarded as illustrative rather than limiting and that it is understood that the following claims including all equivalents are intended to define the scope of the invention.

We claim:

1. A removable stent for temporarily supporting a region of a vessel in a body comprising:
   a stent portion comprised of:
     an elongate perfusable vessel supporting portion adapted to be configurable between a reduced size for placement in the vessel and removal therefrom and an expanded size for structurally supporting the vessel in the region; and
     perfusable end portions connected to and forming ends of said vessel supporting portion and adapted to allow fluid flow therethrough,
     and further in which said stent portion is comprised of a plurality of helically wound flat wires forming an elongate hollow tube in which the cross sectional dimension of the flat wires in the radial direction is less than the cross sectional dimension of the flat wires in the tangential direction; and
   an actuator portion having a proximal end extending out of the body and a distal end connected to said stent portion and operable by manipulation at said proximal end to configure said support portion into said reduced size and said expanded size.

2. The temporary stent of claim 1 in which the elongate hollow tube of said stent portion comprises:
a proximal end and a distal end and further in which movement of said distal end toward said proximal end causes expansion of the diameter of said hollow tube and movement of said proximal end away from said distal end causes contraction of the diameter of the hollow tube.

3. The temporary stent of claim 2 in which said actuator portion comprises:
a first elongate member comprising an elongate catheter tube connected to said proximal end of said stent portion, and
a second elongate member slidably disposed in a lumen of said first elongate member and extending to and operable to move said distal end of said stent portion with respect to said proximal end of said stent portion.

4. The stent of claim 3 in which said elongate catheter tube comprises:
an outer tubular layer, and
an inner tubular layer concentric with said outer tubular layer.

5. The stent of claim 4 in which a distal end of said inner tubular layer terminates proximally from the distal end of said outer tubular layer and further in which said outer tubular layer has a reduced diameter distally from the distal end of said inner tubular layer.

6. The stent of claim 3 in which said second elongate member further comprises:
a guidewire tip extending distally from the distal end of said stent portion.

7. The stent of claim 6 in which said second elongate member is connected to the distal end of said stent portion.

8. The stent of claim 6 in which said second elongate member is slidingly received in the distal end of said stent portion and further in which said second elongate member comprises:
a first bearing portion operable to move said distal end of said stent portion distally; and
a second bearing portion operable to move said distal end of said stent portion proximally.

9. The stent of claim 6 in which said plurality of helically wound wires when said stent portion is in said expanded size comprise:
a proximal tapered region connected to said first elongate member:
and a distal tapered region connected to said second elongate member and further in which said plurality of helically wound wires forming the stent portion in said proximal tapered region and said distal tapered region are spaced apart from wires adjacent thereto to provide relatively large openings through said proximal and said distal tapered regions to facilitate blood flow therethrough.

10. The stent of claim 1 in which said plurality of wires are comprised of stainless steel wires.

11. The stent of claim 1 in which said stent portion comprises at least in part a fluoroscopic detectable material.

12. The stent of claim 11 in which said fluoroscopic detectable material is selected from a group consisting of: gold, tantalum, platinum, tungsten and tungsten-iridium alloy.

13. The stent of claim 1 in which said second elongate member comprises:
an inner catheter member having a lumen therewithin extending from a proximal end of said inner catheter member to an opening at the distal end of said inner catheter member.

14. The stent of claim 13 in which said second inner catheter member is dimensioned so that fluids may be introduced to the distal end of said first elongate member via the lumen of said first elongate member in which said second catheter member is located.

15. The stent of claim 1 in which said actuator portion comprises at least in part a fluoroscopic detectable material.

16. The stent of claim 15 further comprising:
at least one band composed of a fluoroscopically detectable material connected to said actuator portion.

17. The stent of claim 16 in which said coating is selected from a group consisting of urokinase, heparin, albumen protein and antithrombin III.

18. The stent of claim 1 in which said stent portion is comprised at least in part of a material having non-thrombogenic properties.

19. The stent of claim 18 in which said stent portion includes a coating of a material comprising a slow release non-thrombogenic polymer.

20. The stent of claim 18 further comprising a DC source having a lead connected to said stent portion and another lead connectable to a patient's body.

21. A method of temporarily implanting a stent into a region of the vascular system of a patient comprising the steps of:
advancing an expandable stent portion of the stent to the region,
operating an actuator portion comprised of a first elongate member having an outer catheter member connected to a proximal end of the stent portion and a second elongate member comprising a tubular member connected to a distal end of the stent portion by moving a proximal end of the first elongate member with respect to a proximal end of the second elongate member to cause expansion of the stent portion by moving a proximal end of the stent portion relatively to a distal end of the stent portion relatively to a distal end of the stent portion to effect expansion of a diameter of the stent,
supporting the region of the vascular system with the stent portion and allowing perfusion through the stent portion while in the stent portion is in an expanded configuration,
operating an actuator portion to cause contraction of the stent portion, and
withdrawing the stent portion.

22. The method of claim 21 in which the second elongate member comprises an inner catheter member having a lumen therein and further comprising the steps of:
positioning a guidewire in the vascular system of the patient to the region to be supported by the stent,
advancing the stent portion, the outer catheter member, and the inner catheter member into the region of the vascular system over the guidewire through the lumen in the inner catheter member.

23. The method of claim 22 further comprising the step of:
introducing fluids to the vascular system via the lumen of the inner catheter member.

24. The method of claim 22 further comprising the step of:
   introducing fluids to the vascular system via a lumen of the outer catheter member.

25. The method of claim 21 further comprising the steps of:
   positioning a delivery catheter into the patient to the region of the vascular system of the patient; and
   advancing the stent portion and the actuator portion to the region of the vascular system through a lumen in the delivery catheter.

26. The method of claim 21 further comprising the steps of:
   connecting a lead of a voltage source to the stent portion,
   connecting another lead to the body of the patient, and
   applying a potential between the leads to minimize the tendency for clotting materials to form on the stent portion.

27. The method of claim 21 in which said stent portion has a length of approximately between 1.5 and 3.5 cm when in an expanded size.

28. The method of claim 27 in which said stent portion has a length of approximately between 2.5 and 5 cm when in a reduced size.

29. The method of claim 21 in which said stent portion has a length of approximately between 2.5 and 5 cm when in a reduced size.

30. The method of claim 29 in which said stent portion has a length of approximately between 1.5 and 3.5 cm when in an expanded size.

31. The method of claim 21 in which said stent portion is comprised a plurality of helically wound wires.

32. The method of claim 21 in which said stent portion in an expanded configuration has a ratio of length to diameter of between 3.75 and 17.5.

33. The method of claim 21 in which said stent portion in an expanded configuration has a ratio of length to diameter of greater than 3.75.

34. A removable stent for temporarily supporting a region of a vessel in a body comprising:
   (a) a stent portion comprised of:
      (1) an elongate perfusable vessel supporting portion adapted to be configurable between a reduced size for placement in the vessel and removal therefrom and an expanded size for structurally supporting the vessel in the region; and
      (2) perfusable end portions connected to and forming ends of said vessel supporting portion and adapted to allow fluid flow therethrough; and
   (b) an actuator portion having a proximal end extending out of the body and a distal end connected to said stent portion and operable by manipulation at said proximal end to configure said support portion into said reduced size and said expanded size and further in which said actuator portion comprises:
      (1) a first elongate member comprising an elongate catheter tube connected to said proximal end of said stent portion, said elongate catheter tube comprised of:
         (A) an outer tubular layer; and
         (B) an outer tubular layer concentric with said outer tubular layer; and
      (2) a second elongate member slidably disposed in a lumen of said first elongate member and extending to and operable to move said distal end of said stent position with respect to said proximal end of said stent portion.

35. The stent of claim 34 in which a distal end of said inner tubular layer terminates proximally from the distal end of said outer tubular layer and further in which said outer tubular layer has a reduced diameter distally from the distal end of said inner tubular layer.

36. The stent of claim 34 in which said stent portion is comprised a plurality of helically wound wires forming an elongate hollow tube.

37. The stent of claim 36 in which said plurality of helically wound wires when said stent portion is in said expanded size comprise:
   a proximal tapered region connected to said first elongate member:
   and a distal tapered region connected to said second elongate member and further in which said plurality of helically wound wires forming the stent portion in said proximal tapered region and said distal tapered region are spaced apart from wires adjacent thereto to provide relatively large openings through said proximal and said distal tapered regions to facilitate blood flow therethrough.

38. The stent of claim 34 in which said stent portion is comprised a plurality of helically wound flat wires forming an elongate hollow tube in which the cross sectional dimension of the flat wires in the radial direction is less than the cross sectional dimension of the flat wires in the tangential direction.

39. The stent of claim 34 in which said second elongate member comprises:
   an inner catheter member having a lumen therewithin extending from a proximal end of said inner catheter member to an opening at the distal end of said inner catheter member.

40. The stent of claim 34 in which said second inner catheter member is dimensioned so that fluids may be introduced to the distal end of said first elongate member via the lumen of said first elongate member in which said second catheter member is located.

41. The stent of claim 34 in which said stent portion is comprised at least in part of a material having nonthrombogenic properties.

42. A method of temporarily implanting a stent into a region of the vascular system of a patient said stent comprised of an expandable stent portion and an actuator portion formed of an outer catheter member connected to a proximal end of the stent portion and an inner catheter member having a lumen therein connected to a distal end of the stent portion, said method comprising the steps of:
   positioning a guidewire in the vascular system of the patient to the region to be supported by the stent,
   advancing the expandable stent portion, the outer catheter member, and the inner catheter member of the stent to the region over the guidewire through the lumen in the inner catheter member, said stent portion having a generally cylindrical size when expanded for structurally supporting the vessel in the region,
   operating the actuator portion to cause expansion of the stent portion by moving a proximal end of the outer catheter member with respect to a proximal end of the inner catheter member to move a proximal end of the stent portion relatively to a distal end of the stent portion to effect expansion of a diameter of the stent, supporting the region of the vascular system with the stent portion and allowing perfusion through the stent portion while in the stent portion is in an expanded configuration, operating the actuator portion to cause contraction of the stent portion, and withdrawing the stent portion.

43. The method of claim 42 further comprising the step of:

introducing fluids to the vascular system via the lumen of the inner catheter member.

44. The method of claim 42 further comprising the step of:

introducing fluids to the vascular system via a lumen of the outer catheter member.

45. A method of temporarily implanting a stent into a region of the vascular system of a patient comprising the steps of:

positioning a delivery catheter into the patient to the region of the vascular system of the patient; and advancing the stent portion and the actuator portion to the region of the vascular system through a lumen in the delivery catheter, said stent portion having a generally cylindrical size when expanded for structurally supporting the vessel in the region, operating an actuator portion to cause expansion of the stent portion, supporting the region of the vascular system with the stent portion and allowing perfusion through the stent portion while in the stent portion is in an expanded configuration, operating an actuator portion to cause contraction of the stent portion, and withdrawing the stent portion.

46. A method of temporarily implanting a stent into a region of the vascular system of the patient comprising the steps of:

advancing an expandable stent portion of the stent to the region, said stent portion having a generally cylindrical size when expanded for structurally supporting the vessel in the region, operating an actuator portion to cause expansion of the stent portion, supporting the region of the vascular system with the stent portion and allowing perfusion through the stent portion while in the stent portion is in an expanded configuration, connecting a lead of a voltage source to the stent portion, connecting another lead to the body of the patient, and applying a potential between the leads to minimize the tendency for clotting materials to form on the stent portion, operating an actuator portion to cause contraction of the stent portion, and withdrawing the stent portion.

* * * * *